US00PP08521P

United States Patent [19]

Trees

[11] Patent Number: Plant 8,521

[45] Date of Patent: Dec. 28, 1993

[54] GERANIUM PLANT 'SHOWCASE RED'

[75] Inventor: Scott C. Trees, Nipomo, Calif.

[73] Assignee: Ball Floraplant, West Chicago, Ill.

[21] Appl. No.: 996,111

[22] Filed: Dec. 23, 1992

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 5,933 4/1987 Schumann ..... Plt. 87.12

P.P. 6,708 3/1989 Duemmen ..... Plt. 87.12

P.P. 7,959 9/1992 Hanes ..... Plt. 87.12

*Primary Examiner*—James R. Feyrer

*Attorney, Agent, or Firm*—Arnold, White & Durkee

[57] ABSTRACT

Geranium Showcase Red is a new and distinct cultivar of geranium, botanically known as *Pelargonium*×*hortorum* Bailey. It is distinguished from other geranium plants by good basal branching, compact mounded habit, freely flowering character and particularly by its self-branching without use of growth regulators.

1 Drawing Sheet

BACKGROUND OF THE NEW PLANT

Showcase Red is a product of a planned breeding program which had the objective of creating new geranium cultivars with compact habit, dark green foliage, freely flowering, fast rooting, good shipping qualities, and self-branching without use of growth regulators.

Showcase Red was originated from a hybridization made in a controlled breeding program in West Chicago, Ill. The female parent was Plaisire (U.S. Plant Pat. No. 6,708), a plant with a semi-double, medium salmon flower with medium foliage with light zone. The male parent of Showcase Red was Tango (U.S. Plant Pat. No. 5,933), a plant with dark green foliage and a semi-double, scarlet-red flower.

Showcase Red was discovered and selected as one flowering plant within the progeny of the stated cross by the inventor in a controlled environment in Santa Maria, Calif. Showcase Red differed from both parents in the color of the flower and in its self-branching characteristics.

By comparison with the pollen parent Tango, Showcase Red has a more compact basal branching habit and a more upright growth habit. Showcase Red flowers 5–7 days earlier in the greenhouse than Tango. Tango generally has 1–2 petaloids in each floret which are larger than the 3–4 various size petaloids displayed by Showcase Red.

Basal branching is exhibited by Showcase Red without pinching or use of growth regulators. The parent Tango has less branching by comparison while the seed parent Plaisire has basal branching comparable to Showcase Red. Typically, Showcase Red will have 2–3 basal branches in a 10 cm pot in the greenhouse while the pollen parent Tango will have 1–2 branches and the seed parent Plaisire will show 3–4 branches when grown under the same conditions.

The first act of asexual reproduction of Showcase Red was accomplished when vegetative cuttings were taken from the initial selection in a controlled environment in Santa Maria, Calif. by a technician working under the supervision of the inventor. Horticultural examination of selected units demonstrated that the combination of characteristics as herein disclosed for Showcase Red are firmly fixed and are retained through successive generations of asexual reproduction.

Showcase Red has not been observed under all possible environmental conditions. The phenotype may vary significantly with variations in environment such as temperature, light intensity, and day length. The following observations, measurements and comparisons describe plants grown in Arroyo Grande, Calif. under greenhouse conditions which approximate those generally used in commercial practice.

Of the many commercial cultivars known to the present inventor, the most similar in comparison to Showcase Red is Eclipse Red (U.S. Plant Pat. No. 7,959).

Both plants have red flowers of the same general tonality and generally similar foliage form. However, showcase red is more compact in habit, somewhat shorter in height by an average of 2–3 cm, has no color zonation compared to Eclipse Red's distinct color zonation, exhibits somewhat fewer flowers per umbel, has a smaller corolla diameter and has a hemispherical bud shape in comparison with the pointed oval bud shape typical of Eclipse Red. Also in contrast to Eclipse Red, the new cultivar sets no fruits while Eclipse Red sets fruit occasionally in field trials.

The flowers of Showcase Red give the overall effect of having a "white eye". This is not shown in Eclipse Red or the pollen parent Tango. The effect is caused by the gradation of a general red tone at the base of each petal, petaloid and filament to nearly white. Further characteristics of Showcase Red differing from Eclipse Red include:

1. Showcase Red has 3–4 petaloids of various sizes, generally smaller in size than those of Eclipse Red.
2. Average diameter of each Showcase Floret is b 4.0–4.5 cm which is somewhat smaller than the average diameter of Eclipse Red florets (4.8–5.0 cm).
3. Showcase Red is flatter in appearance than Eclipse Red which has larger petaloids giving it a more double appearance.
4. The general leaf color of Showcase Red (139A abaxial, 137C adaxial) is darker than Eclipse Red which does not exhibit the pronounced leaf zone observed in Eclipse Red (136A leaf margin, 136B leaf base).

DESCRIPTION OF THE PHOTOGRAPH

The accompanying color photographs show a top view of the typical flower and foliage characteristics of Showcase Red. The view taken against a dark background illustrates flower color closest to the color values assigned from the Royal Horticultural Society Colour Chart. The view taken against a light background highlights the leaf characteristics.

DESCRIPTION OF THE PLANT

In the following description, color references are made to the Royal Horticultural Society Colour Chart. The color values were determined between 12:00–12:15 p.m. on Nov. 10, 1992 under 600 foot candles at Arroyo Grande, Calif. USA.

The following traits have been repeatedly observed and are determined to be basic characteristics of Showcase Red which in combination distinguish this geranium as a new and distinct cultivar. These characteristics include a self-branching, compact habit obtained without the use of growth regulators, a period of 49 days to first flower from unrooted direct stock, a plant height of 20.5 cm and a plant width of 28.0 cm at the time of first flower.

Classification:

*Botanical.*—*Pelargonium* × *hortorum* Bailey.

*Commercial.*—Showcase Red, Zonal Geranium.

INFLORESCENCE

Umbel:

*Average diameter.*—10.5–11.0 cm.

*Average depth.*—7.5–8.0 cm.

*Peduncle length.*—10.0–11.0 cm.

*Pedicel length.*—4.3 cm.

*Number umbels/plant (designate circumstances.)*—13–15 on 18 week old field grown plant.

*Number of flowers/umbel.*—24–27.

Corolla:

*Average diameter.*—4.0–4.5 cm.

*Form.*—Semi-double with petaloids of various sizes.

*Number of Petaloids.*—3–4.

*Color (General tonality from a distance of three meters).*—Red: base of each petal, petaloid, and filament grades from a general red tone to nearly white giving the overall effect of a white eye.

*Description of petal form.*—Non-imbricate.

*Color (abaxial).*—44B.

*Color (adaxial).*—44C.

*Number of petals.*—5.

*Petal size.*—Width: 1.7–2.4 cm. Length: 2.6–2.8 cm.

Bud:

*Shape.*—Hemispherical.

*Color (abaxial)*—44B.

*Color (adaxial)*—44C.

Reproductive organs:

*Androecium.*—10, 9 mm. anther/filaments 1.0–1.8 mm anther.

*Gynoecium.*—3 mm style.

*Presence or absence of fruits.*—No fruits.

Spring flowering response period: 49 days from unrooted cuttings in greenhouse.

Outdoor flower production:

*Floriferous.*—Continuous flowering.

Durability: High degree of weather tolerance.

Foliage:

*Form.*—Reniform, cordate base.

*Margin.*—Crenate.

*Color (abaxial).*—139A.

*Color (adaxial).*—137C.

*Color (zonation).*—None.

*Tolerance of botrytis.*—Some tolerance.

*Internode length.*—1.5–1.8 cm.

*Size.*—8.0–9.0 cm at widest point to 5.0–5.75 cm at narrowest point.

*Zonation.*—Not obvious on plants grown in green house but slight zonation apparent under high light outdoor growing conditions (see drawing).

*Leaf pedicles (stems).*—6.5–7.5 cm on mature leaves.

General appearance and form:

*Internode length.*—1.5–1.8 cm.

*Branching pattern.*—Good basal branching.

*Height.*—20.5 cm at first flower in greenhouse, compact mounded habit.

What is claimed is:

1. A new and distinct geranium cultivar, substantially as herein described and shown, characterized by its compact habit and self-branching without the use of growth regulators.

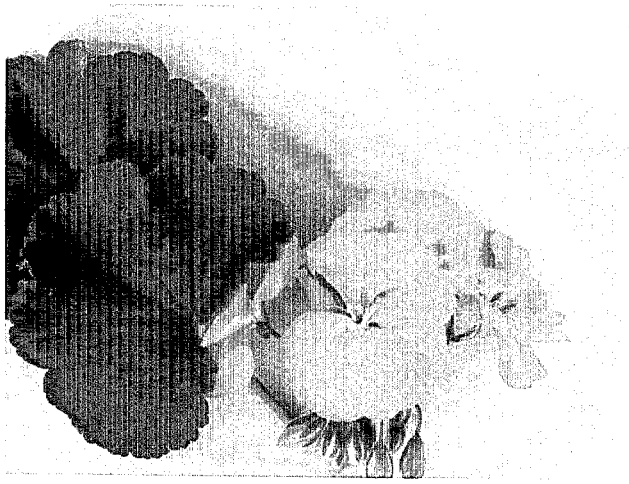
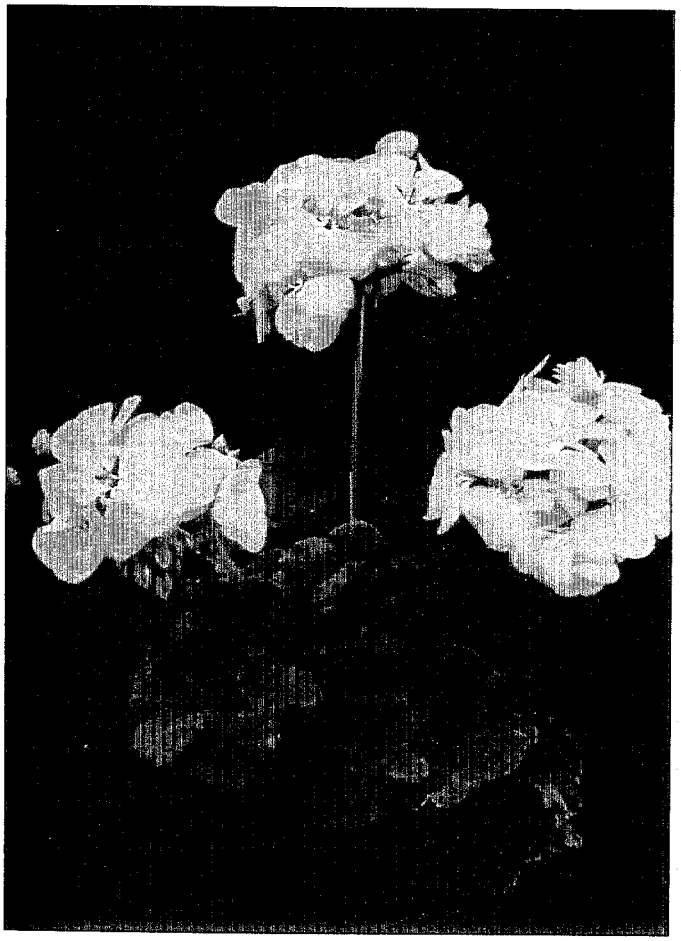

* * * * *